US007943389B2

(12) United States Patent
Rigsby

(10) Patent No.: US 7,943,389 B2
(45) Date of Patent: May 17, 2011

(54) METHOD FOR DETERMINING CHLORINE DEMAND IN WATER

(75) Inventor: Karen Rigsby, Woodstock, GA (US)

(73) Assignee: Chemtura Corporation, Middlebury, CT (US)

( * ) Notice: Subject to any disclaimer, the term of this patent is extended or adjusted under 35 U.S.C. 154(b) by 758 days.

(21) Appl. No.: 11/514,003

(22) Filed: Aug. 30, 2006

(65) Prior Publication Data

US 2007/0082405 A1 Apr. 12, 2007

Related U.S. Application Data

(60) Provisional application No. 60/724,586, filed on Oct. 7, 2005.

(51) Int. Cl.
*G01N 33/22* (2006.01)
(52) U.S. Cl. ............ 436/125; 422/408; 422/61; 23/230; 424/661; 424/723; 514/241; 514/247; 514/387; 514/389; 436/102; 436/119; 436/124
(58) Field of Classification Search .................. None
See application file for complete search history.

(56) References Cited

U.S. PATENT DOCUMENTS

| | | | | |
|---|---|---|---|---|
| 3,413,199 A | | 11/1968 | Morrow, Jr. | |
| 4,049,382 A | * | 9/1977 | Ross et al. | 205/780 |
| 5,011,613 A | * | 4/1991 | Feray et al. | 210/739 |
| 5,464,636 A | * | 11/1995 | Hight et al. | 424/661 |
| 5,683,654 A | | 11/1997 | Dallmier et al. | |

FOREIGN PATENT DOCUMENTS

| | | |
|---|---|---|
| AU | 749656 | 6/2002 |
| JP | 2001 179264 | 7/2001 |

OTHER PUBLICATIONS

Sandrolini et al. (Cement and Concrete Research 31 (2001) 485-489.*
Che Mical Abstract: 141:282290 Field Testing the Chlorine Wall Demand in Distribution Mains. American Water Works Assoc. (2003).
Chemical Abstract : 139:122294 "Determination of Chlorine Demand in Water and Wastewater" Water Services & Technology (2003).
Chemical Abstract : 126:268120 "Automation of Long Term Chlorine Demand Measurement" Water Research (1977).
Chemical Abstract : 116:221181 Chlorine Demand A.
Chemical Abstract: 93:173516 "Residual Chlorine Analysis" Water Works (1977).
Chemical Abstract: 80:40856 "Semi quantitative Determination of Chlorine Dosages for Water Treatment using Pattern-Recognition Techniques" American Water Works (1973).
Chemical Abstract: 76:117375 "Continuous Method of Monitoring Water Quality by Chlorine Consumption under Ultraviolet Radiation" Water Research (1972).
Chemical Abstract: 64:34366 "Determination of Free Chlorine by Methyl Orange" American Water Works Assoc. (1965).
Chemical Abstract: 55:107707 "Graphical and Mathematical Interpretations for Chlorine Determinations" Water Pollution Control Federation (1961).
Chemical Abstract: 48:22963 "Continuous Recording of Chlorine Residuals and Determination of Chlorine Demand" Symposium on Continuous Analysis of Industrial Water and Industrial Waste Water (1952).
Abstract: 46:55389 "The Determination of the Chlorine-binding Power and Excess Chlorine-binding Power of Drinking Water . . . " Pharmazeutische Zentralhalle fuer Deutschland (1952).
Chemical Abstract : 46:15634 "Determination of Chlorine Demands and Chlorine Residuals in Sewage" Sewage and Industrial Wastes (1951).
Chemical Abstract: 38:2707 "An Accurate Direct Quick Method for the Determination of Cl in Water and Sewage Containing Interfering Substances" Chemiker-Zeitung (1943).
Chemical Abstract: 35:48996 "A Multiple Nomograph for Chlorine Demand Determinations" Water Works and Sewerage (1940).
Chemical Abstract: 32:1652 "A Modification of the Chlorine Demand Test and the o-tolidine Test for Residual Chlorine in Sewages" Sewage Works Journal (1937).
Chemical Abstract: 26:29012 "Brun's Method of Determining the amount of Chlorine Necessary for Water Disinfection" Dept.Sci.Ind. Research-Water Pollution (1930).
Chemical Abstract: 25:19802 "Method of Determination of the Chlorine Demand of Any Water" Paper Mill (1931).
Chemical Abstract: 25:19802 "Method of Determination of the Chlorine Demand of Any Water" Paper Mill (1931).
Chemical Abstract: 98:77888 "Determination of Chlorine Demands" Toshiba Corp. Japan.
Chemical Abstract: 84:169341 "Determining the Chlorine Demand of Water by Ultraviolet Irradiation" Agency of Industrial Sciences and Technology, Japan.
Chemical Abstract: 77:92717 "Measurement and Control of Dissolved Chlorine in Water" Chlorination Equipment Ltd. U.K.
Chemical Abstract: 014279779 "Chlorine Demand Measurement Involves Injecting Sodium Hypochlorite Solution into Test Water . . . "Patent Assignee: Nisshin Electrical Co.Ltd.
Chemical Abstract: 013448897 "Chlorine Demand Meter of Waterworks Installation . . . "Patent Assignee: Nisshin Electrical Co. Ltd.
Chemical Abstract: 010918127 "Determination of Chlorine Demand for Free-Flowing or Static Water . . . ." Patent Assignee: WRC PLC.

(Continued)

*Primary Examiner* — Sally A Sakelaris
(74) *Attorney, Agent, or Firm* — Joseph Suhadolnik

(57) ABSTRACT

Methods for determining chlorine demand in water are provided. One method comprises (a) providing a test water sample containing at least one contaminant and a source of chlorine and a source of bromide; (b) heating the test water sample for a suitable time and temperature sufficient to substantially oxidize the at least one contaminant in the test water sample; and (c) determining the content of residual chlorine present in the test water sample.

15 Claims, No Drawings

OTHER PUBLICATIONS

Chemical Abstract: 010109801 "Water Quality Control System for Effective Control" Patent Assignee: Toshiba KK.
Chemical Abstract: 009538174 "Apparatus for Measuring Chlorine Demand" Patent Assignee: Japan Carlit Co. Ltd.
Chemical Abstract: 008368868 "Controlling Free Residual Chlorine Content of Drinking Water . . . "Patent Assignee: SOC Lyonnaise Eaux L'Eclairage (Lyon, France).
Chemical Abstract: 001651079 "Determining Chlorine Demand of Water by UV Irradiation" Patent Assignee: Agency of Ind. Sci. & Technology.
Chemical Abstract: 121286221 "Usefulness of Measurements of UV Absorbance of Waters" Facultad de Ciencias, Universidad de Cordoba, Spain. (1994).
Chemical Abstract: 93:173516 "Residual Chlorine Analysis—Significance of Results" American Water Works (1977).
Chemical Abstract: 55:77904 "Comparison of Chlorine—Determination Methods in Waste Waters" Journal Water Pollution Control Federation (1961).
Chemical Abstract: 36:45159 "Oxidation-Reduction Potential as a Measure of the Effectiveness of the Chlorination of Water" Chem. Zentr (1941).
Chemical Abstract: 33:45547 "The Chlorine 'Test' in the Chlorination of Water" Congr.Chim.Ind., Compt.rend.18me congr. Nancy (1938).
Chemical Abstract: 13:4013 "Determination of the Amount of Chlorine Required for Purification of Water" Comptes Rendus des Seances de la Societe de Biologie et de Ses Filiales (1918).
Chemical Abstract: 11:10817 "Determination of the Quantity of Javel Extract Required in Purification of Water" Journal de Pharmacie et de Chimie (1917).
Chemical Abstract: 135:322474 "Method and Apparatus for Measurement of Chlorine Required Amount in Water Purification" Nissin Electric Co. Ltd., Japan.
Chemical Abstract: 133:48609 "Meter for Measurement of Required Chlorine Amount for Water Purification" Nissin Electric Co. Ltd., Japan.

* cited by examiner

METHOD FOR DETERMINING CHLORINE DEMAND IN WATER

PRIORITY

This application claims the benefit under 35 U.S.C. §119 to U.S. Provisional Application 60/724,586, filed on Oct. 7, 2005, and entitled "METHOD FOR DETERMINING CHLORINE DEMAND IN WATER", the contents of which are incorporated by reference herein.

BACKGROUND OF THE INVENTION

1. Technical Field

The present invention generally relates to a method for determining chlorine demand in water.

2. Description of the Related Art

In order to insure that the water in a pool or spa is safe, it must be properly sanitized to prevent any health problems arising due to such contaminants as, for example, algae, bacteria, or any other pathogens which may be in the water. Thus, it is the goal of any owner or operator of recreational water bodies, swimming pools, spas, hot tubs or the like to provide pool water which is maintained so that there are no detrimental contaminants. To this end, the pool owner or operator may choose from a wide variety of biocidal chemical systems to ensure that a biocidally effective amount of water-treating agents is present in the water body on a continuous basis.

The more commonly used biocidal agents are chlorine-containing biocides. The chlorine can be in a number of different forms, e.g., sodium hypochlorite (liquid bleach), calcium hypochlorite, lithium hypochlorite, chlorinated isocyanurates, etc. When any of these materials interact with water, they undergo hydrolysis to form free chlorine consisting of predominantly hypochlorous acid (HOCl), which is the sanitizing agent, and hypochlorite ion.

In order to determine whether the amount of chlorine present is adequate to effect disinfection, measurements are made beyond the chlorine input point. The amount of chlorine added to the water is ordinarily referred to as the "dosage," and is usually expressed as parts per million (ppm). The amount of chlorine used up or consumed by the contaminants, e.g., bacteria, algae, organic compounds and some inorganic substances, such as iron or manganese, is designated as the "demand." Since many of the reactions with chlorine are not instantaneous, but require time to reach completion, chlorine demand is time-dependent.

The amount of chlorine remaining in the water at the time of measurement is referred to as the "residual chlorine." Residual is therefore determined by the dosage subtracted from the demand. Inasmuch as chlorine demand is time-dependent, this dependency is likewise true of chlorine residual.

When chlorine dissolves in water, a mixture of hypochlorous and hydrochloric acids is formed. Actually, the hydrochloric acid always completely dissociates into hydrogen and chloride ions, whereas the hypochlorous acid only partially dissociates into hydrogen and hypochlorite ions. In either the hypochlorous acid or hypochlorite ion form, chlorine is called "free chlorine residual." Free chlorine residual has a highly effective killing power toward bacteria.

The National Spa and Pool Institute recommends 1 to 3 parts per million of residual chlorine in water and a pH between 7.2 and 7.8. Presently, chlorine demand testing in pool water samples has been performed by preparing a stock solution of chlorine, dosing a control sample of distilled water and a test pool water sample and then allowing the samples to incubate. However, this method is relatively slow as it ordinarily takes eight to twenty-four hours for the samples to incubate.

Accordingly, it would be desirable to provide an improved method for determining chlorine demand in water, e.g., pool and spa water, such that a suitable amount of chlorine is present in the water to ensure, for example, proper sanitation of the water.

SUMMARY OF THE INVENTION

A method for determining chlorine demand in water is provided. In one embodiment of the present invention, a method for determining chlorine demand in water comprises:

(a) providing a test water sample containing at least one contaminant and a source of chlorine and a source of bromide;

(b) heating the test water sample for a suitable time and temperature sufficient to substantially oxidize the at least one contaminant in the test water sample; and (c) determining the content of residual chlorine present in the test water sample.

In accordance with a second embodiment of the present invention, a method for determining chlorine demand in water is provided, the method comprising:

(a) adding simultaneously or sequentially a source of chlorine and a source of bromide to a test water sample containing at least one contaminant;

(b) heating the test water sample for a suitable time and temperature sufficient to substantially oxidize the at least one contaminant in the test water sample; and (c) determining the content of residual chlorine present in the test water sample.

In another embodiment, the foregoing methods can further comprise comparing a result from the determining step to a result obtained from a control sample.

In accordance with a third embodiment of the present invention, a kit for determining chlorine demand in a representative sample of water is provided comprising:

(a) a source of chlorine and a source of bromide; and
(b) means for heating the water sample.

By incorporating a source of bromide, e.g., a bromide salt, in addition to using heat, it is believed that oxidation of contaminant(s) present in a test water sample occurs much more rapidly thus allowing the incubation time to be substantially reduced, e.g., to about thirty minutes. Accordingly, the methods of the present invention advantageously allow an individual to have water, e.g., pool or spa water, tested for chlorine demand in an expeditious manner as compared to the prior art method to determine how much additional chlorine, if any, should be added to the water in order to maintain the recommended amount of chlorine. In this manner, the water will contain a sufficient amount of chlorine to properly sanitize the water.

DETAILED DESCRIPTION OF THE PREFERRED EMBODIMENTS

The present invention is directed to methods for determining chlorine demand in water. Generally, the water to be tested can be, for example, pool water, spa water and the like. The water will ordinarily contain at least one contaminant such as, for example, ureas, proteins, creatinine, ammonia, amino acids, organic contaminants such as plants, leaves, algae, suntan oil, cosmetics, fertilizers and the like and combinations thereof. The contaminants normally found in water are well known to one skilled in the art and are capable of undergoing oxidation.

In one embodiment of the present invention, the method for determining chlorine demand in water includes at least:

(a) providing a test water sample containing at least one contaminant and a source of chlorine and bromide ions;

(b) heating the test water sample for a suitable time and temperature sufficient to substantially oxidize the contaminants in the test water sample; and (c) determining the content of residual chlorine present in the test water sample.

In step (a) of the method of the present invention, a source of chlorine and a source of bromide are added to a test water sample, e.g., pool water or spa water. The source of chlorine and bromide can be any source of chlorine and bromide ions that would introduce free chlorine and bromide into the test water sample. A useful source of chlorine ions includes, but is not limited to, sodium dichloroisocyanurate, trichloroisocyanurate, sodium hypochlorite, lithium hypochlorite, calcium hypochlorite and the like and mixtures thereof. A useful source of bromide ions includes any bromide salt such as, for example, potassium bromide, sodium bromide and the like and mixtures thereof.

Generally, the source of chlorine and source of bromide can be added simultaneously or sequentially to the test water sample. For example, a first stock solution containing distilled water and a source of chlorine and a second stock solution containing distilled water and a source of bromide can be added simultaneously or sequentially to the test water sample. Alternatively, a stock solution containing distilled water and both a source of chlorine ions and source of bromide ions can be added directly to the test water sample. The amount of the source of chlorine and source of bromide present in the test water sample will vary according to the individual carrying out the test and is within the purview of one skilled in the art.

It is particularly advantageous to employ a control sample in the methods of the present invention. For example, a control sample can be prepared containing, e.g., distilled water, and substantially no contaminants and then adding the same source of chlorine and source of bromide that were added to the test water sample in the substantially same amounts as discussed above.

In step (b) of the method of the present invention, the test water sample and control sample are heated for a suitable time and temperature sufficient to substantially oxidize the at least one contaminant in the test water sample. It is believed that by adding the source of bromide ions to the test water sample together with the source of chlorine ions and heating the test water sample, the contaminants will oxidize more quickly. The temperature source for heating the test water sample can be any known source that would normally heat the water sample thoroughly. For example, the source can be a heated water bath, bunsen burner, and the like. The temperature will ordinarily range from about 50° C. to about 80° C. The time period for heating the test water sample will vary, e.g., from about 15 to about 25 minutes. Once the sample has been heated to a temperature sufficient to substantially oxidize the contaminant(s) present in the sample, the test sample and control sample are then allowed to cool to room temperature.

In step (c) of the method of the present invention, the free chlorine residual present in the test water sample can be determined by techniques well known in the art, e.g., iodometric titration method, spectrothotometric methods, test strips, etc. For example, an excess of potassium iodide can be added to the sample and the pH adjusted with, for example, acetic acid or citric acid. The sample can then be titrated with sodium thiosulfate and the color of the sample will change from a brown/yellow color to clear. If desired, a starch indicator can be used. The volume of titrant used for the control sample can then be compared to the volume of titrant used for the test water sample. After the residual chlorine content is determined, the ppm chlorine demand can be calculated by one skilled in the art based on such factors as, for example, the concentration of the sodium thiosulfate used to titrate. The dosage for the pool can then be calculated by one skilled in the art based on such factors as, for example, size of the pool, the amount of water in the pool, etc.

In another embodiment of the present invention, a kit is provided containing the apparatus and/or reagents necessary to carry out the foregoing test method in the field. A complete kit would contain all of the equipment and consumables for conducting at least one test procedure. Thus, such a kit would include a device for obtaining a test sample of water, e.g., a pipette or syringe for drawing the water sample, at least one device for holding a precise volume of the water sample, e.g., a flask or column, a source of chlorine, e.g., sodium dichloroisocyanurate, a source of bromide, e.g., potassium bromide, and a means for heating the test sample, e.g., a warming vessel. The source of chlorine and bromide can be provided in powder form, either in one container or in separate containers, along with a device for holding a precise volume of the source of chlorine and bromide. In this manner, the user of the kit can simply add distilled water to the device to obtain a stock solution. Alternatively, the source of chlorine and bromide can be provided as a stock solution. If desired, other reagents can be included such as, for example, a quantity of base with which to adjust the pH of the sample to within the alkaline region and a quantity of acid with which to readjust the pH of the sample. A partial test kit would include, at a minimum, the aforesaid source of chlorine and source of bromide.

The following non-limiting example is illustrative of the method of the present invention.

EXAMPLE

The following procedure was used to determine the amount of chlorine needed to be added to pool water to maintain the recommended level according to the method of the present invention.

Procedure

1. A chlorine demand stock solution was prepared by weighing 12 grams of sodium dichloroisocyanurate and diluting to 1000 mls in a flask. The flask was then capped and stored in the dark.

2. A potassium bromide (KBr) stock solution was prepared by weighing approximately 110 mg of KBr and diluting it to 1000 mls.

3. A control sample was prepared by measuring 100 mls of distilled water and emptying it into a 250 ml Erlenmeyer flask. Next 5.0 mls of each stock solution was added into the flask using a pipet.

4. For each sample, 100 mls of pool water was measured into a 250 ml Erlenmeyer flask. Next, 5.0 mls of each stock solution was added into each sample using a pipet and the flask was covered.

5. The test samples and control sample were placed into a water bath at a temperature of 50° C. to 55° C. for 20 minutes.

6. After 20 minutes, the samples were removed from the water bath and allowed to sit at room temperature for 10 minutes.

7. Next, approximately 1 gram of potassium iodide and approximately 1 ml of acetic acid were added to each flask and stirred to mix. If chlorine was present, a brown color would appear.

8. Using 0.1N sodium thiosulfate, the samples were titrated dropwise (while stirring) until the solution turned a light yellow color.

9. To each flask was added approximately 1 ml of starch indicator. The sample was titrated dropwise (while stirring) until the solution turned clear and the number of mls used was recorded.

10. The number of mls used to titrate the samples was subtracted from the number of mls used to titrate the control. This number was multiplied by 35.5 and the ppm chlorine demand was recorded.

11. The dosage was calculated as follows:

Demand/5.6=pounds of Burn Out Extreme® per 10,000 gallons of water.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A method for determining chlorine demand in water comprising:
   (a) obtaining a known volume of a test water sample from the water and adding to the test water sample:
      a selected amount of a source of chlorine and
      a selected amount of a source of bromide, followed by
   (b) heating the test water sample to about 50° C. to about 80° C. for about 15 to 25 minutes to oxidize contaminants in the test water sample, followed by
   (c) determining by known techniques the content of residual chlorine present in the test water sample and calculating from the residual chlorine content the chlorine demand for the water.

2. The method of claim 1 wherein the test water sample is obtained from pool or spa water.

3. The method of claim 1, wherein the source of chlorine is selected from the group consisting of sodium dichloroisocyanurate, trichloroisocyanurate, sodium hypochlorite, lithium hypochlorite, calcium hypochlorite and mixtures thereof.

4. The method of claim 1, wherein the source of bromide is a bromide salt.

5. The method of claim 4, wherein the bromide salt is selected from the group consisting of potassium bromide, sodium bromide and mixtures thereof.

6. The method of claim 1, wherein prior to step (c) the test water sample is cooled to room temperature prior to determining the content of residual chlorine.

7. The method of claim 1, wherein the content of residual chlorine in the test water sample is determined by iodometric titration.

8. The method of claim 1, further comprising comparing a result from step (c) to a result obtained from a control sample containing substantially no contaminants which has been treated according to steps (a), (b) and (c) in a manner identical to the test sample.

9. The method for determining chlorine demand in water of claim 1 comprising preparing a chlorine source stock solution of sodium dichloroisocyanurate, trichloroisocyanurate, sodium hypochlorite, lithium hypochlorite, calcium hypochlorite or mixtures thereof in water, preparing a bromide source stock solution of potassium bromide, sodium bromide or mixtures thereof in water; and
   (a) adding to a known volume of a test water sample a selected amount of the chlorine source stock solution and a selected amount of the bromide source stock solution, followed by
   (b) heating the test water sample to about 50° C. to about 80° C. for about 15 to about 25 minutes, and
   (c) determining by titration or spetrophotometric techniques the content of residual chlorine present in the test water sample.

10. The method of claim 9, further comprising comparing a result from step (c) to a result obtained from a control sample containing substantially no contaminants which has been treated according to steps (a), (b) and (c) in a manner identical to the test sample.

11. The method of claim 9, wherein the content of residual chlorine in the test water sample is determined in step (c) by an iodometric titration.

12. The method of claim 9, wherein step (a) comprises adding the chlorine source stock solution and the bromide source stock solution simultaneously.

13. The method of claim 9, wherein step (a) comprises adding the chlorine source stock solution and the bromide source stock sequentially.

14. The method of claim 1, wherein step (a) comprises adding the chlorine source and the bromide source simultaneously.

15. The method of claim 1, wherein step (a) comprises adding the chlorine source and the bromide sequentially.

* * * * *